(12) United States Patent
Huffman

(10) Patent No.: US 6,925,208 B1
(45) Date of Patent: Aug. 2, 2005

(54) METHODS AND APPARATUS FOR PARTITIONING TRANSFORM DATA

(75) Inventor: John C. Huffman, Menlo Park, CA (US)

(73) Assignee: Stentor, Inc., Brisbane, CA (US)

(*) Notice: Subject to any disclaimer, the term of this patent is extended or adjusted under 35 U.S.C. 154(b) by 615 days.

(21) Appl. No.: 10/138,956

(22) Filed: May 4, 2002

(51) Int. Cl.$^7$ ................................................ G06K 9/36
(52) U.S. Cl. .................... 382/232; 382/233; 382/305; 382/240; 709/247
(58) Field of Search ................................ 382/232, 299, 382/305, 233, 240; 345/1.2, 3.3; 709/247

(56) References Cited

U.S. PATENT DOCUMENTS

| | | | |
|---|---|---|---|
| 4,222,076 A | 9/1980 | Knowlton | 358/470 |
| 4,751,742 A | 6/1988 | Meeker | 382/240 |
| 4,853,779 A | 8/1989 | Hammer et al. | 375/240.22 |
| 4,943,855 A | 7/1990 | Bheda et al. | 375/240.11 |
| 5,097,331 A | 3/1992 | Chen et al. | 375/240.11 |
| 5,436,447 A | 7/1995 | Shew | 250/291 |
| 5,539,658 A | 7/1996 | Mc.Cullough | 715/730 |
| 5,548,708 A | 8/1996 | Sakashita et al. | 345/501 |
| 5,563,960 A | 10/1996 | Shapiro | 382/239 |
| 5,577,134 A | 11/1996 | Westerink | 382/240 |
| 5,585,852 A | 12/1996 | Agarwal | 375/240.11 |
| 5,600,373 A | 2/1997 | Chui et al. | 375/240.1 |
| 5,602,589 A | 2/1997 | Vishwanath et al. | 375/240.11 |
| 5,604,824 A | 2/1997 | Chui et al. | 382/248 |
| 5,619,998 A | 4/1997 | Abdel-Malek et al. | 600/437 |
| 5,621,660 A | 4/1997 | Chaddha et al. | 709/247 |
| 5,703,965 A | 12/1997 | Fu et al. | 382/232 |
| 5,710,835 A | 1/1998 | Bradley | 382/233 |
| 5,724,070 A | 3/1998 | Denninghoff et al. | 345/547 |
| 5,740,428 A | 4/1998 | Mortimore et al. | 707/104.1 |
| 5,742,892 A | 4/1998 | Chaddha | 725/146 |
| 5,764,807 A | 6/1998 | Pearlman et al. | 382/240 |
| 5,768,535 A | 6/1998 | Chaddha et al. | 709/247 |
| 6,012,083 A | 1/2000 | Savitzky et al. | 709/203 |
| 6,067,383 A | 5/2000 | Taniguchi et al. | 382/240 |
| 6,085,221 A | 7/2000 | Graf | 709/202 |
| 6,314,452 B1 | 11/2001 | Dekel et al. | 709/203 |
| 6,556,724 B1 * | 4/2003 | Chang et al. | 382/299 |
| 6,711,297 B1 * | 3/2004 | Chang et al. | 382/240 |

FOREIGN PATENT DOCUMENTS

| | | | |
|---|---|---|---|
| EP | 0 669 765 A2 | 8/1995 | H04N/7/24 |
| EP | 0 701 375 A2 | 3/1996 | H04N/7/24 |
| WO | PCT/GB96/00623 | 9/1996 | H04N/1/41 |
| WO | PCT/AU97/00724 | 5/1998 | G06T/9/40 |

OTHER PUBLICATIONS

Chee, Y.–Kheong, Survey of Progressive Image Transmission Methods, Imago Multimedia Centre, John Wiley & Sons, 1999, vol. 10,3–19, pps.–17.

Rogge, B., Region of Interest Based Progressive Transmission of Grayscale Images Across The Internet, University of Ghent.

Richard L.Phillips, "A Bridge from Full–Function to Reduced–Function Workstations", I.E.E.E. Computer Graphics and Application May 6, (1986) NY, NY.

* cited by examiner

*Primary Examiner*—Anh Hong Do

(57) ABSTRACT

Transform data is partitioned to more efficiently process requests in a server to transfer source data to a client. The transform data, generated from source data, comprises spatially related coefficients such that a block of coefficients permits reconstruction of identifiable portions of the source data. The transform data is partitioned into a plurality of partitions of coefficients. Each partition consists of coefficients for reconstruction of an identifiable portion of the source data. The client generates a request for one or more partitions of coefficients. The client request is sent to the server. The server extracts the partitions of coefficients set forth in the request, and transfers the partitions of coefficients to the client. Techniques for partitioning of transform data to support lossy compression are disclosed.

14 Claims, 12 Drawing Sheets

Physical Coefficient Blocks = Partition1[addr1], Partition2[addr2], Partition3[addr3], Partition4[addr4], Partition5[addr5], Partition6[addr6], Partition7[addr7]

Virtual Coefficient Blocks = Partition1[Q = 4], Partition2[Q=4], Partition3[Q=4], Partition4[Q=0], Partition5[Q=0], Partition6[Q=0], Partition7[Q=0]

METHODS AND APPARATUS FOR PARTITIONING TRANSFORM DATA

BACKGROUND OF THE INVENTION

1. Field of the Invention

The present invention is directed toward the field of transferring images over a network, and more particularly towards partitioning transform data for efficient transfer of transform data between a server and a client.

2. Art Background

It has become more common for images to be stored, distributed, and viewed in digital form using computer technology. In the medical field Picture Archival and Communication Systems or PACS have been in widespread use. In a typical PACS application, image data obtained by imaging equipment, such as CT scanners or MRI scanners, is stored in the form of computer data files. The size of a data file for an image varies depending on the size and resolution of the image. For example, a typical image file for a diagnostic-quality chest X-ray is on the order of 10 megabytes (MB). The image data files are usually formatted in a "standard" or widely accepted format. In the medical field, one widely used image format is known as DICOM. The DICOM image data files are distributed over computer networks to specialized viewing stations capable of converting the image data to high-resolution images on a CRT display.

In imaging applications, it is important to display images at a high resolution. For example, in the medical imaging application, images require display at high resolution so that image details having potential diagnostic significance are visible. Also, in the medical imaging application, concurrent viewing of multiple images, captured over time, is desirable in order to enable the detection of changes that occur over a time period. The need for high resolution and multiple views translates into a need for high network bandwidth, large storage capacity, and significant processing power at the viewing stations. The traditional digitally encoded medical images, used in medical applications, usually require powerful and expensive computer systems to archive, distribute, manipulate, and display the medical images. Consequently, many current imaging systems, such as PACS, are very expensive. Because of this, a medical center having a PACS may have only a few image viewing stations, used primarily by specialists, such as radiologists.

A technique for distributing large images over a network, such as medical images, has been developed by Dr. Paul Chang, M.D., and Carlos Bentancourt at the University of Pittsburgh. This technique operates in a client-server environment to deliver, from the server to the client, image data as the image data is needed at the client (i.e., a just in time data delivery mechanism). To implement this just in time data delivery mechanism, the dynamic transfer syntax generates a flexible hierarchical representation of an image for storage at the server. The hierarchical representation consists of coefficients produced by a wavelet transform. To view portions of the image at the client, the client issues requests for data that include coefficient coordinates to identify coefficients in the hierarchical representation. The client then reconstructs the portion of the image, at the client, from the transform data requested. A complete description of the dynamic transfer syntax is contained in U.S. Provisional Patent Application, entitled "flexible Representation and Interactive Image Data Delivery Protocol", Ser. No. 60/091,697, inventors Paul Joseph Chang and Carlos Bentancourt, filed Jul. 3, 1998, and U.S. Patent Application, entitled "Methods and Apparatus for Dynamic Transfer of Image Data", Ser. No. 09/339,077, inventors Paul Joseph Chang and Carlos Bentancourt, filed Jun. 23, 1999, both of which are expressly incorporated herein by reference.

Although the above-identified techniques increase the ability to distribute large data files over a network, in some circumstances additional performance is required. The present invention increases performance of data transfer techniques that use transform data by partitioning the transform data, so as to optimize the access and transfer of transform data in a client-server environment.

SUMMARY OF THE INVENTION

Transform data is partitioned to more efficiently process requests in a server to transfer source data to a client. The transform data, generated from source data, comprises spatially related coefficients such that a block of coefficients permits reconstruction of identifiable portions of the source data. The transform data is partitioned into a plurality of partitions of coefficients. Each partition consists of coefficients for reconstruction of an identifiable portion of the source data. The client generates a request for one or more partitions of coefficients. The client request is sent to the server. The server extracts the partitions of coefficients set forth in the request, and transfers the partitions of coefficients to the client. In one embodiment, the server memory maps the partitions of coefficients to individually access the partitions of coefficients.

In one embodiment, the technique supports transfer of lossy coefficients to accommodate client-server sessions with limited bandwidth. For this embodiment, the client includes in the request at least one quantization value for the partition of coefficients. In one embodiment, the server compresses the partitions of coefficients for storage. For this embodiment, the server extracts the compressed partitions of coefficients, and de-compresses the partitions. The server quantizes the partitions of coefficients, in accordance with the quantization value, to generate quantized partitions of coefficients. The server then compresses the quantized partitions of coefficients to generate compressed partitions of coefficients. At the client, the compressed partitions of coefficients are de-compressed to recover the partitions of coefficients.

The techniques for partitioning of transform data also support transmitting residual coefficients from the server to the client. For this embodiment, the client generates a second request for partitions of coefficients identified in a prior request. The prior request identified a first quantization value for the partition of coefficients, and the second request identified a second quantization value for the partition of coefficients. The server, upon receipt of the request, extracts the partition of coefficients identified in the second request, quantizes the partitions of coefficients in the second request, in accordance with the second quantization value, to generate second quantized partitions of coefficients, and generates a second compressed partition of coefficients from the second quantized partitions of coefficients. The client receives the second compressed partition of coefficients, retrieves a first quantized partition of coefficients from a cache, and de-compresses the second compressed partition of coefficients to generate the second quantized partition of coefficients. The client then generates a first and a second de-quantized coefficient blocks by multiplying the first and second quantized partition of coefficients by the first and second quantization values, respectively. An aggregate partition of coefficients is generated by adding the first de-quantized partition of coefficients with the second de-quantized partition of coefficients. Source data is reconstructed from the aggregate partition of coefficients.

BRIEF DESCRIPTION OF THE DRAWINGS

FIG. 2b illustrates level three and level four decompositions for the 4K×4K source image of FIG. 2a.

DETAILED DESCRIPTION

A technique is used to partition transform data to effectuate the transfer of source data in a client-server environment. Source data, such as images, are transformed to spatially related coefficients. Specifically, the source data is decomposed into one or more hierarchical data representations, also referred to herein as pyramidal data representations. In general, the transform, a sub-band decomposition function, retains the spatial characteristics between the original source data and the resultant coefficients of the transform data. Thus, the coefficients from the transform data are readily identifiable for subsequent reconstruction of the original source data or any portion of the source data. In other embodiments, a quantized technique is used with the partitioned transform data for limited bandwidth applications.

Figure 1:
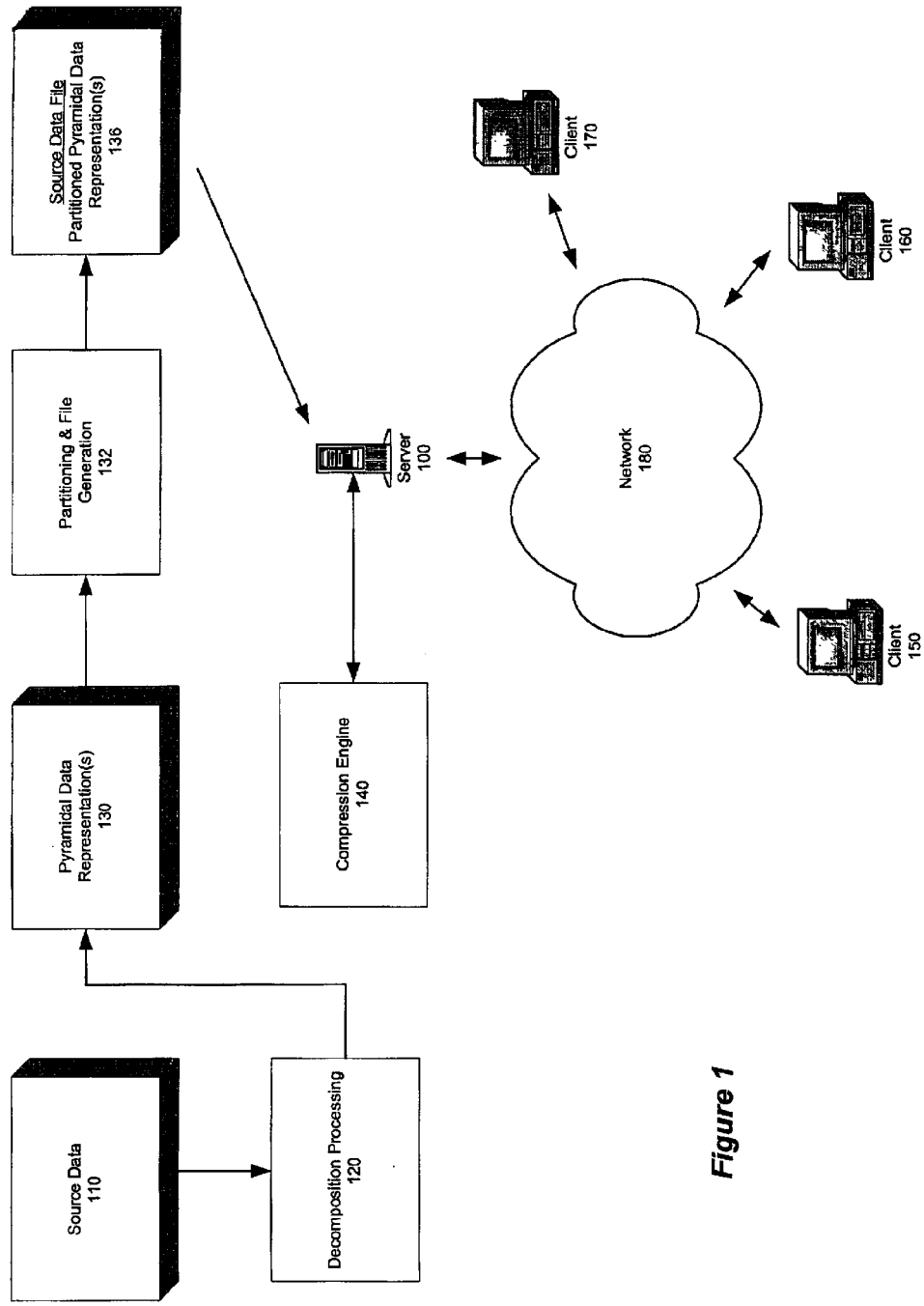
FIG. 1 is a block diagram illustrating one embodiment for processing source data.

FIG. 1 is a block diagram illustrating one embodiment for processing source data. For this embodiment, source data 110 is processed for distribution to a plurality of clients (i.e., clients 150, 160 and 170). In one embodiment, source data 110 comprises one or more source images. If source data 110 comprises images, then the source images 110 are processed for distribution over network 180 for display on client computers (150, 160 and 170). For the embodiment of FIG. 1, source data 110 is input to decomposition processing 120. In general, decomposition processing 120 executes a wavelet transform to generate the pyramidal data representations 130. In a preferred embodiment, the source data is "preprocessed" and stored in the hierarchical or pyramidal data representation. The pyramidal data representation(s) 130 are the further processed by the partitioning and file generation processing 132 to generate a source data file 136. The source data file 136 includes the pyramidal data representation(s) (i.e., physical coefficients), organized into partitions, and information to identify the location of the levels in the pyramidal data representation(s) as well as information to identify the location of the physical coefficients of the individual partitions within the levels. As shown in FIG. 1, server 100 has access to the source data file 136. Also, the server 100 has access to the compression engine 140. In one embodiment, the decomposition processing 120, partitioning & file generation 132, and compression engine 140 comprises software operating on server 100.

The spatially related transform for the decomposition function may be generally defined as:

$$\hat{W}I = X,$$

wherein: $\hat{W}$ defines the transform function for a transform that generates spatially related coefficients; I represents the source data (e.g., image); and X represents the transformed data (e.g., transformed image).

In general, in a spatial transform, the information is aggregated so as to preserve the predictability of the geometry of the source image. For example, using a wavelet or sub-band transform, specific coefficients of the transform data may be identified that contribute to specific geometric features of the source image (i.e., a pre-defined portion of a source image is directly identifiable in the transform data).

The use of the wavelet transform to generate the pyramidal data structure provides a scalable solution for transferring different portions of a large data file. When the source image 110 is decomposed into the pyramidal data structure 130, sub-images and sub-resolution images, in the granularity of partitions of coefficients, are extracted directly from disk of the server for optional response. The image server then transmits only the partitions of physical coefficients, or quantized partitions of coefficients for low bandwidth applications, required to reconstruct the exact size of the desired image for display at the client. Accordingly, the multi-resolution format is implicit in the pyramidal data structure.

In general, the pyramidal data structure 130 comprises a hierarchical representation of the source image. Each level of the hierarchical representation is sufficient to reconstruct the source image at a given resolution. In one embodiment, the decomposition processing 120 utilizes a sub-band decomposition to generate the hierarchical representation. In general, the process of sub-band decomposition consists of executing a process to separate "high-pass" information from "low-pass" information. For the sub-band decomposition embodiment, decomposition processing 120 comprises a finite impulse response (FIR) filter.

The wavelet transform function embodiment generates mathematically independent information among the levels of the hierarchical representation. Accordingly, there is no redundant information in the pyramidal data structure 130. Thus, pyramidal data structure 130 is not merely multiple replications of the source image at different resolutions, but it contains unique data at the different levels of the hierarchical representation. The mathematically independent nature of the wavelet transform permits minimizing the amount of data transferred over a network, by requiring only the transfer of "additional data" not yet transferred to the computer from the server necessary to construct a given image. The wavelet transforms are lossless, in that no data from the original source image is lost in the decomposition into the pyramidal data structure 130. Accordingly, the transform has applications for use in medical imaging and medical imaging applications.

In one embodiment, fixed-point kernels are used in the wavelet transform (i.e., decomposition processing 120). The use of fixed-point kernels generates coefficients for the pyramidal data structure that permit an easy implementation into a standard pixel footprint. In one embodiment, the wavelet transform is a spatial transform that generates a dynamic range of the "low low" component equal to the dynamic range of the source image. Because of this characteristic, the "low low" component does not contain overshoot or undershoot components. As a result, the use of fixed-point kernels is preferred because no normalization process to convert the transformed dynamic range to the pixel dynamic range is required.

In one embodiment, the image transfer system directly utilizes the transform coefficients as pixels, without re-scaling the coefficients. The range of the high-pass components (i.e., "low high", "high low", and "high high" components) is the range of the input source data plus up to two bits per coefficient (e.g., 1 bit for "LH" and "HL" and 2 bits for "HH"). This characteristic permits mapping of all components (i.e., high and low pass components) to a given pixel footprint.

In other embodiments, the wavelet transform may be used to generate multi-spectral transform data. In general, multi-spectral transform data aggregates multi-components of the source image into a vector for the transform data. Also, the multi-spectral transform data may comprise any type of attribute for binding to the source image, such as color variations and/or non-visual components (e.g., infrared components).

In yet other embodiments, the wavelet transform may be used to generate multi-dimensional data (e.g., two dimensional, three dimensional, etc.) for a source image. For example, multi-dimensional transform data may be used to reconstruct a source image in three dimensions.

In general, to generate the pyramidal data structure 130, the transform is applied across the columns, and then this transform, or a different transform, is applied across the rows (i.e., or vice versa). The selection of the transform for decomposition processing 120 is dependent upon the particular characteristics of the pyramidal data structure desired. Each level of the pyramidal data structure is generated by recurring on the low-pass, "low low", of the previous higher level. This recursion continues until a predetermined size is obtained. For example, in one embodiment, the lowest level in the pyramidal data structure for a source image consists of a low-pass component of approximately 128×128. However, any granularity of resolution may be generated for use in a pyramidal data structure without deviating from the spirit or scope of the invention. Also, any quadrant may be used in the recursion process with any desired transform.

Figure 2A:
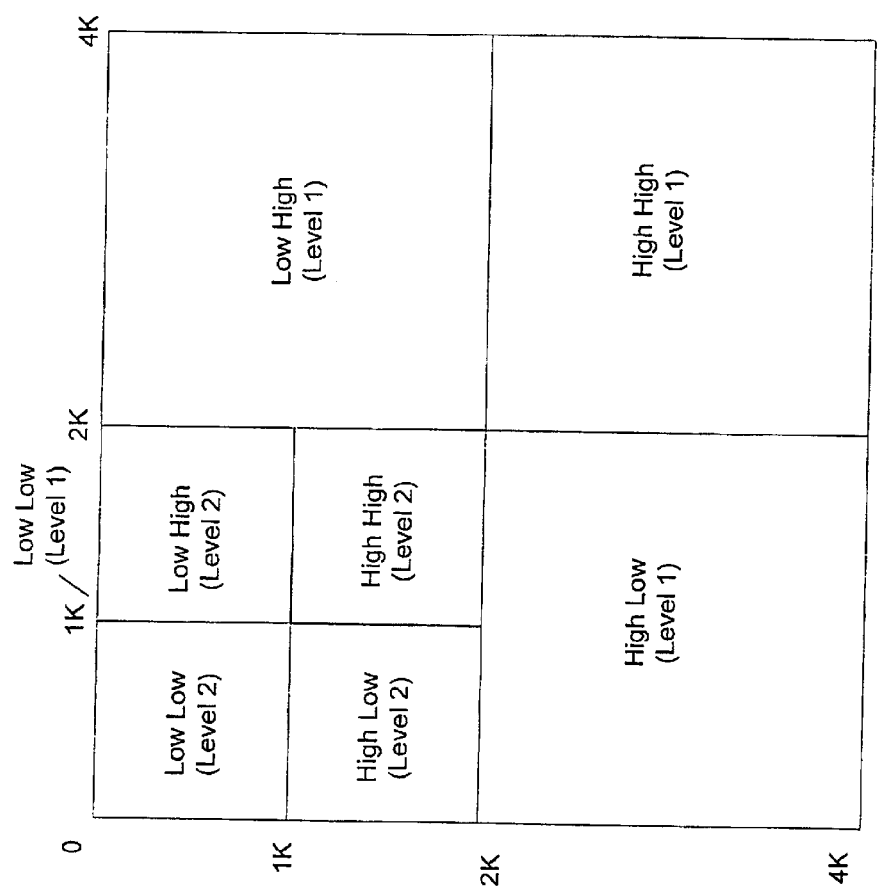
FIG. 2a illustrates an example of a pyramidal data structure.

FIG. 2a illustrates an example of a pyramidal data structure. For this example, the source image comprises a 4K×4K image. The decomposition processing 120 generates, in a first iteration, a level one Mallat structure. Specifically, as shown in FIG. 2a, a low-pass component, "low low", is generated and consists of a 2K×2K sub-image. The high-pass components, consisting of "low high", "high high", and "high low", contain physical coefficient coordinates (e.g., the upper right hand coordinate for the rectangle that constitutes the "low high" component is (4K, 0)).

Figure 2B:
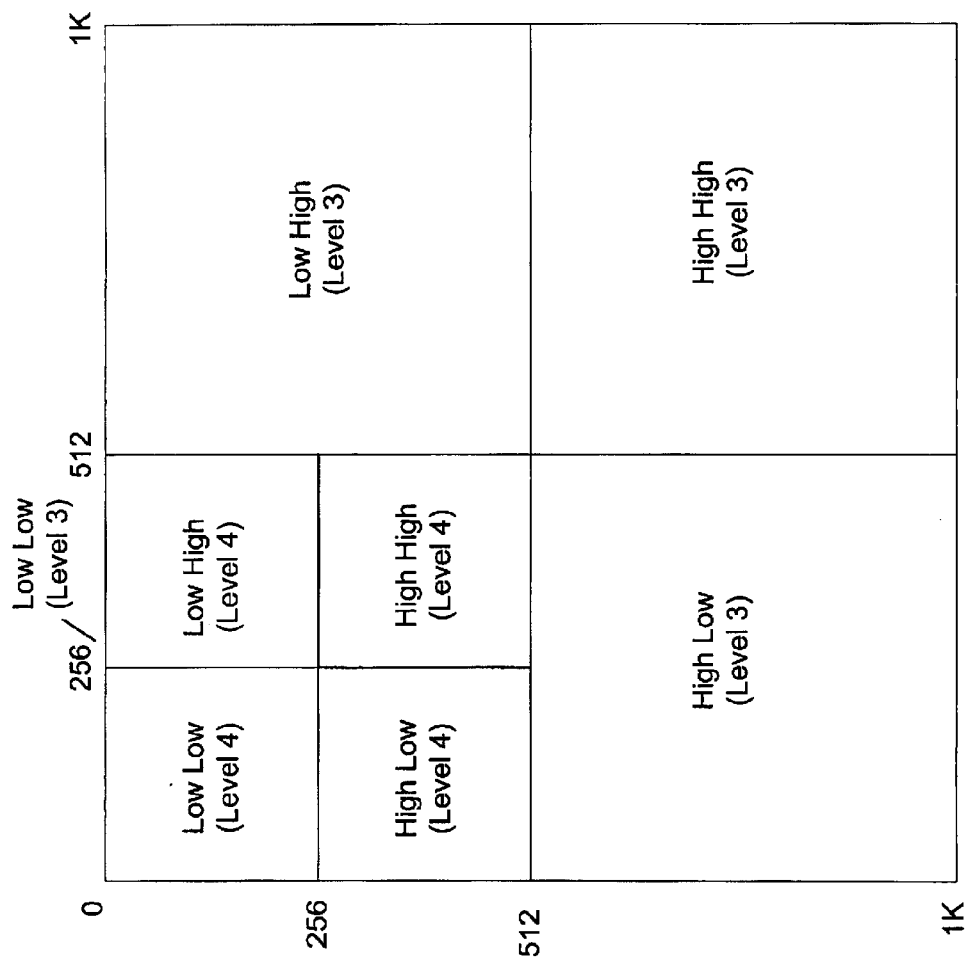

FIG. 2a also illustrates a second level decomposition. The second iteration of decomposition processing 120 operates on the low pass (i.e., "low low"), component of the level one data. For the second level, the low-pass component, "low low", consists of a 1K×1K sub-image, as labeled in FIG. 2a. FIG. 2b illustrates level three and level four decompositions for the 4K×4K source image of FIG. 2a. To generate the level three decomposition, decomposition processing 120 operates on the level two "low low" component (i.e., the 1K×1K image). For the level three transform, the low-pass component, "low low", is a 512×512 sub-image as labeled on FIG. 2a. FIG. 2b also illustrates a fourth level of decomposition for the 4K×4K source image. For the level four transform, the low-pass component comprises a sub-image of 256×256 pixels.

Figure 2C:
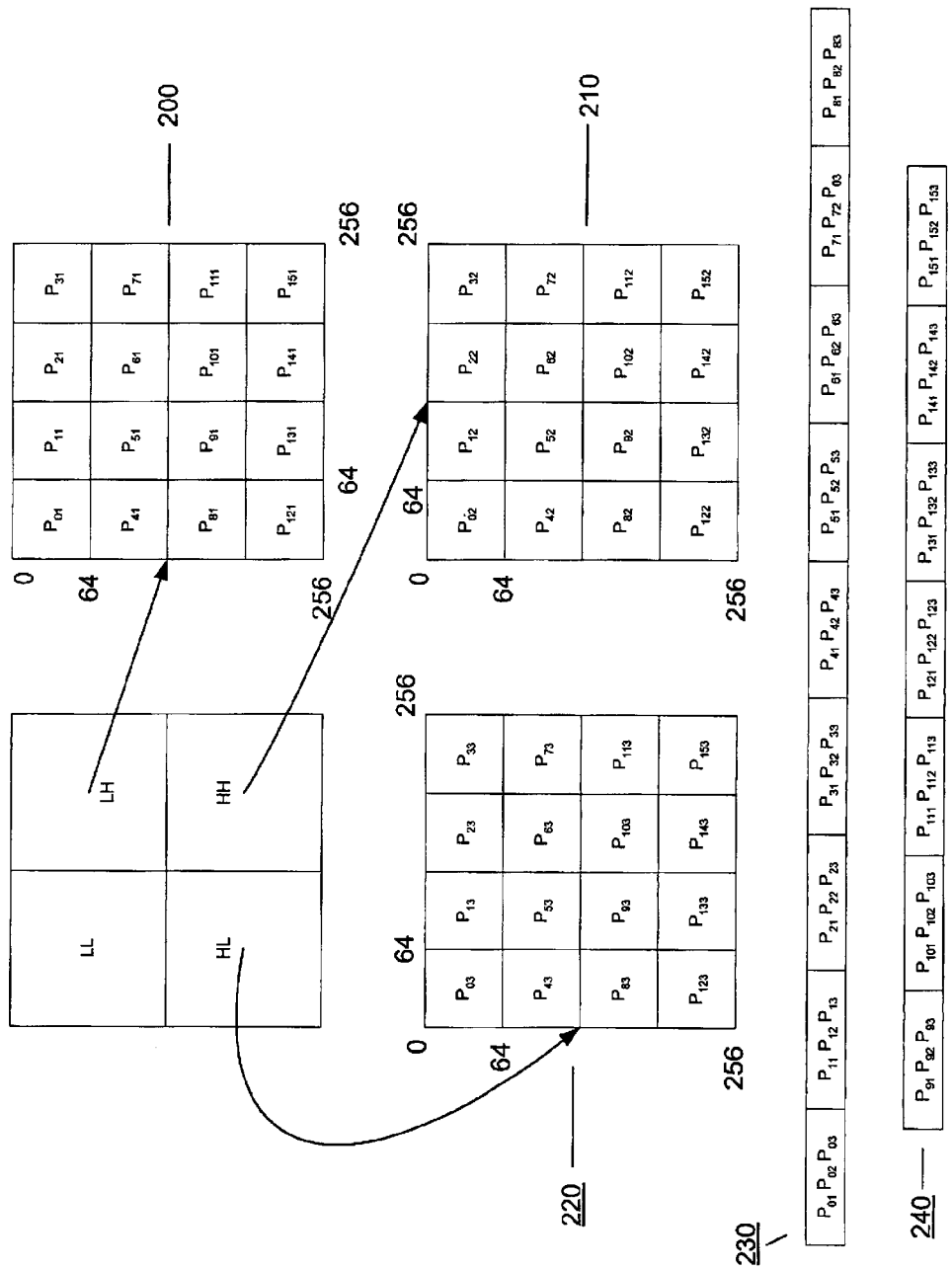
FIG. 2c illustrates organizing a level of a pyramidal data structure in partitions.

The technique of the present invention organizes the coefficients in partitions. FIG. 2c illustrates organizing a level of a pyramidal data structure in partitions. For this example, the coefficients are organized into 64×64 coefficient partitions. In one embodiment, the coefficients consist of signed sixteen (16) bit values, so as to coincide with pixel data. In another embodiment, the coefficients consist of thirty-two (32) bit integer values as required for precision. In other embodiments, the coefficient values may comprise any type of format, such as thirty-two (32) bit floating point. For this example, the coefficients in the high pass components of the level (e.g., low-high (LH), high-low (HL), and high—high (HH)) are each partitioned into 16 partitions (i.e., 256×256 coefficients per component). Although the example of FIG. 2c is shown as partitioning coefficients into 64×64 coefficient blocks, any partition size may be used without deviating from the spirit or scope of the invention. In other embodiments, different levels may use different sized partitions. Each level of the pyramidal data representation above level "n" is organized into partitions (e.g., levels 1, 2, and 3 for the example in FIGS. 2a and 2b).

As shown in FIG. 2c, each partition is uniquely identified. The group of partitions for the LH component, labeled 200 in FIG. 2c, are identified as partitions $P_{01}$–$P_{151}$. Similarly, the group of partitions for the HH component (210) are identified as partitions $P_{02}$–$P_{152}$, and the group of partitions for the HL component (220) are identified as partitions $P_{03}$–$P_{153}$. In one embodiment, the coefficient blocks are organized in a file format as shown in blocks 230 and 240 of FIG. 2c. For this example, the file format organizes the coefficient data by grouping partitions from the LH, HH, and HL components. Thus, for this example, to store this level of coefficient data, partition $P_{01}$ from the LH component is followed by partition $P_{02}$ from the HH component and subsequently by partition $P_{03}$ from the HL component. Similarly, partition $P_{11}$ from the LH component is followed by partition $P_{12}$ from the HH component and subsequently by partition $P_{13}$ from the HL component.

In one embodiment, the wavelet kernel utilized is derived from D. LeGall and A. Tabatabai, (See "Sub-band coding of digital images using symmetric short kernel filters and arithmetic coding techniques," IEEE International Conference on Acoustics, Speech and Signal Processing, New York, N.Y., pp. 761–765, 1988). Any sub-band kernel or pyramid transform could be used within the infrastructure described herein; however, an integer kernel with no coefficient growth in the low pass term has particular advantages in that the low pass coefficients can be used without processing as pixels, and the transform can be inverted exactly in the integer domain. Although floating point kernels have superior signal transfer characteristics, the additional processing required to use these coefficients as pixels, and the need for additional storage to guarantee perfect reconstruction works to their disadvantage. Any sub-band kernel may be used without deviating from the spirit or scope of the invention.

The kernel consists of a low pass and a high pass biorthogonal filter. With input defined as $\{d_j\}$ and $[x]$ defined as the floor function, the forward transform is:

$$\text{Low}[j]=[(d_{2j}+d_{2j+1})/2]$$

$$\text{High}[2]=d_{2j}-d_{2j+1}+\text{Poly}[j]$$

$$\text{Poly}[j]=[(3*\text{Low}[j-2]-22*\text{Low}[j-1]+22*\text{Low}[j+1]-3*\text{Low}[j+2]+32)/64]$$

The inverse transform, used to reconstruct the image, is:

$$d_{2j}=\text{Low}[j]+[(\text{High}[j]-\text{Poly}[j]+1)/2]$$

$$d_{2j+1}=\text{Low}[j]-[(\text{High}[j]-\text{Poly}[j])/2]$$

A more complete description of the spatial transform is contained in U.S. Provisional Patent Application, entitled "Flexible Representation and Interactive Image Data Delivery Protocol", Ser. No. 60/091,697, inventors Paul Joseph Chang and Carlos Bentancourt, filed Jul. 3, 1998, and U.S. Patent Application, entitled "Methods and Apparatus for Dynamic Transfer of Image Data", Ser. No. 09/339,077, inventors Paul Joseph Chang and Carlos Bentancourt, filed Jun. 23, 1999, and assigned to the assignee of the present invention, Stentor, Inc., both of which are expressly incorporated herein by reference.

The techniques of the present invention have application for use in imaging, including medical imaging applications. For this application, a source image is decomposed to generate one or more pyramidal data representations of the source image. Specifically, for the medical imaging application, medical images (e.g., mammogram, X-Ray, MRI, CATSCAN, etc.) are digitized and decomposed to generate pyramidal data representations of the digitized medical images. Medical imaging applications require lossless transmission of data. Because the transform is lossless, no information regarding the original digitized medical image is discarded. Thus, the transform techniques are applicable to medical imaging.

Figure 3:
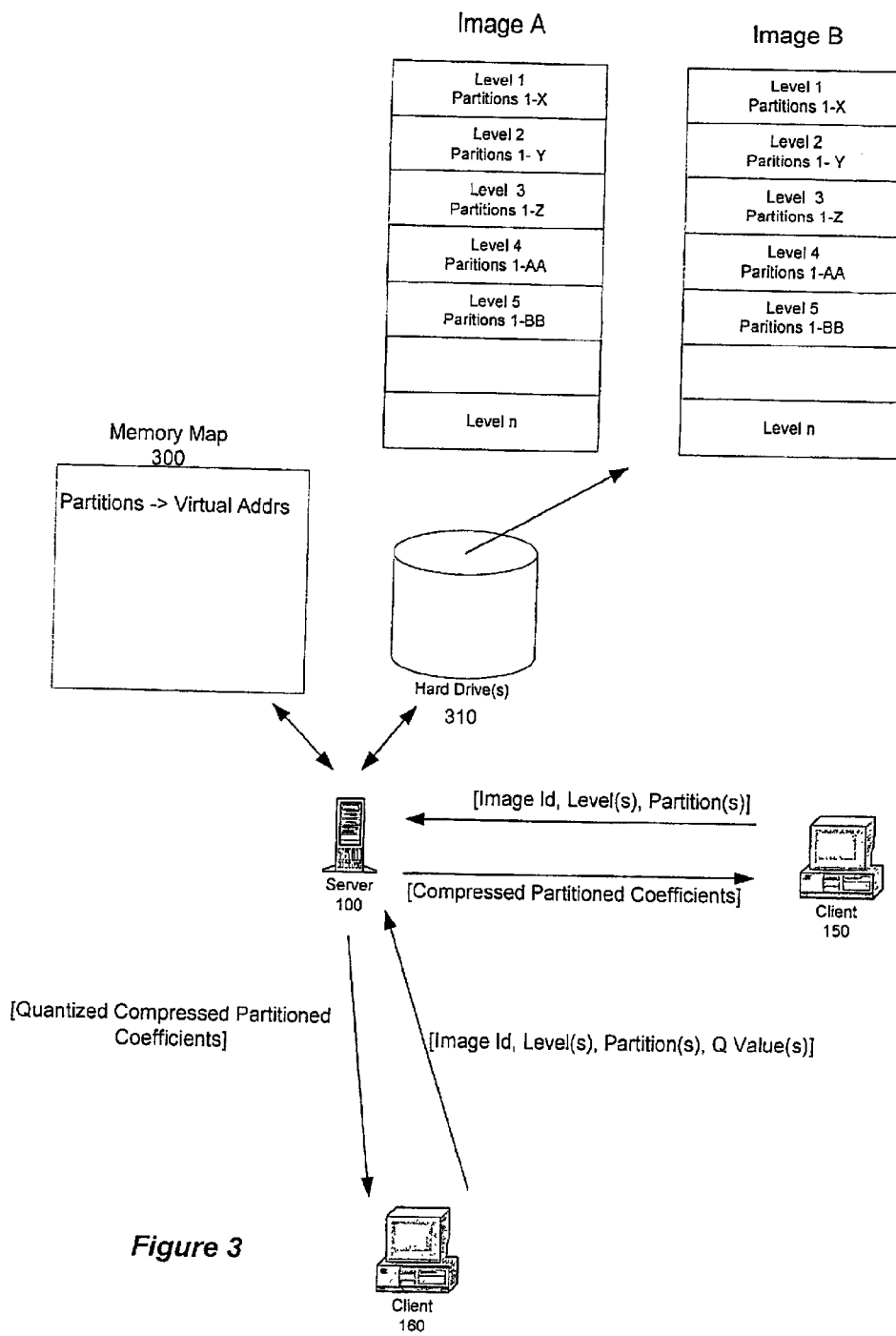
FIG. 3 is a block diagram illustrating one embodiment for implementing the partitioned techniques in a client-server environment.

FIG. 3 is a block diagram illustrating one embodiment for implementing the compression techniques in a client-server environment. For this embodiment, a server 100 is coupled, via a network, to one or more clients (e.g., clients 150 and 160). As shown in FIG. 3, source data 110, for Image A and Image B, is decomposed into "n" pyramidal data representation(s) levels. Also, as shown in FIG. 3, the server 100 accesses the pyramidal data representations 130 for the source data 110. In some embodiments, the server 100 further consists of a compression engine 140. In general, the compression engine 140 compresses, using a lossless encoder technique, the pyramidal data representation(s) 130.

During set up of a communications protocol between the server and the client, the client may specify one or more source data or images (i.e., pyramidal data representations) for the subsequent client request—server transfer process. Alternatively, the client may identify, as part of the request, specific source data or source images for data transfer. In one embodiment, the server-client implements "event" communication services offered through the Common Object Request Broker Architecture ("CORBA"). However, any network protocol may be used to implement client-server network communications without deviating from the spirit or scope of the invention.

For the embodiment of FIG. 3, data is transferred from the server 100 to a client upon the initiation of client requests. Specifically, a client generates a request that identifies one or more partitions of a pyramidal data representation(s) for a source datum or source image. In one embodiment, the client generates a request that defines partitions of coefficient coordinates sufficient to reconstruct the desired portion of the source data at the client. In other embodiments that employ lossy compression, the client specifies a quantization value, Q, to define the level of quantization. In general, the level of quantization, defined by Q, determines the amount of lossy compression (i.e., a greater quantization value yields the loss of a greater amount of information). Thus, there is a trade-off between the loss of information and the compressibility of the data.

In response to the request, the server 100 extracts the partitions of coefficients, identified in the request, losslessly compresses the partitions of coefficients, and transfers the compressed partitions of coefficients to the client. For the quantized embodiment, the server 100 quantizes the partitions of coefficients in accordance with the quantization value contained in the request, losslessly compresses the partitions of coefficients, and then transmits the compressed transform data to the client. This client-server process shown in FIG. 3 depicts both client 150 and client 160 obtaining partitions of coefficients from server 100.

As depicted in FIG. 3, the pyramidal data representations (e.g., Image A and Image B), are stored in a permanent storage medium, such as one or more hard disk drives in server 100. Also, each level of the pyramidal data representation is organized into partitions (e.g., level 1 has "X" partitions, level 2 has "Y" partitions, level 3 has "Z" partitions, level 4 has "AA" partitions, and level 5 has "BB" partitions).

For this example, client 150 generates requests for physical coefficient partitions, and client 160 generates requests for quantized partitions of coefficients. The client request for coefficients includes an image ID (e.g., image A or image B) that identifies one or more levels in the pyramidal data representation and identifies one or more partitions within the levels. In response to the client request, server 100 transmits the partitioned blocks of coefficients to client 150. The client request for client 160, which generates requests for quantized coefficient partitions, includes the image ID, an identification of one or more levels of the pyramidal data representation, an identification of one or more partitions within those levels, and an identification of the quantization values for those partitions identified. For this example, server 100 transmits to client 160, in response to the client's request, the quantized partitioned coefficients identified in the request.

In one embodiment, the server 100 memory maps locations of partitions of coefficients to generate responses to client requests. The memory map technique results in an efficient technique for transferring large data files because the use of volatile memory to store the coefficients is not required.

Figure 4:
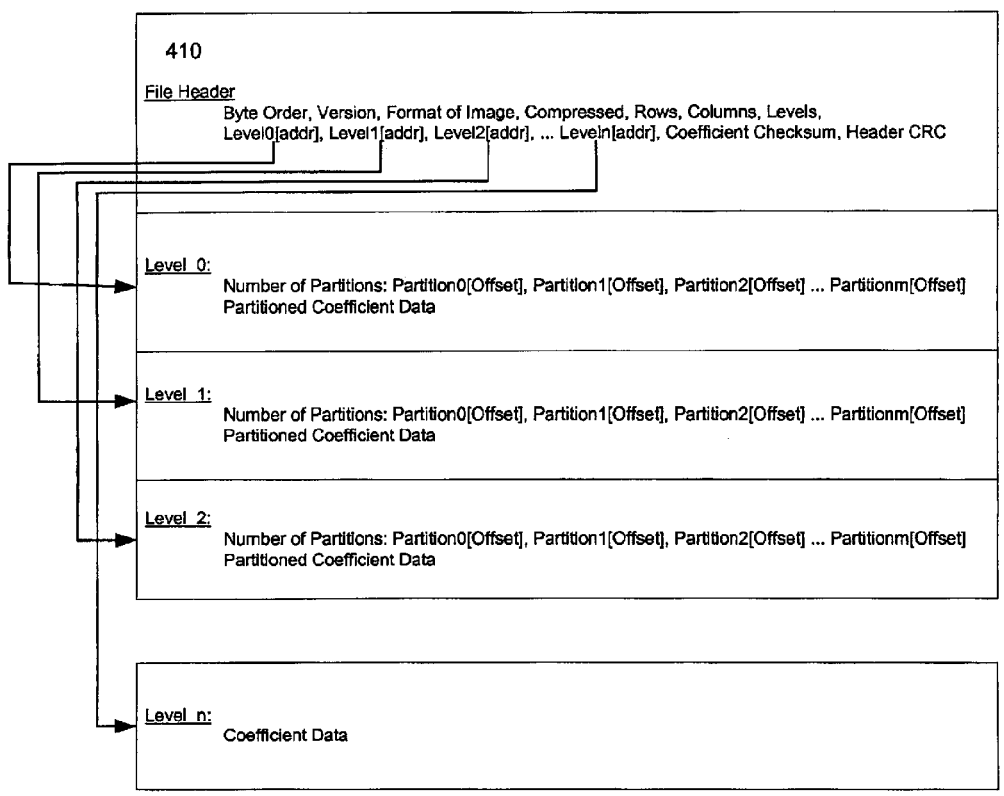
FIG. 4 illustrates one embodiment for a source data file.

FIG. 4 illustrates one embodiment for a source data file. For this embodiment, a source data file 400 includes a file header 410. The file header 410 includes general information about the source data file, as well as pointers to locations to identify levels within the source data file. For this embodiment, the file header 410 specifies: a byte order, version, format of image, compressed partitions, the number of rows, columns, and levels for the corresponding source data, the location of the level offsets, the coefficient checksum, and header CRC. The format of the image may comprise any number of suitable formats for storing images. For example, the image format may include monochrome, luminance/chrominance representations, as well as various types of encoding schemes (e.g., RLE, JPEG, etc.)

As shown in FIG. 4, file header 410 includes addresses to identify locations in the file for each individual level. For this example, level 0[addr] points to a location in source data file 400 for the start of data pertaining to level 0, level 1[addr] points to the starting location in source data file 400 for level 1 data, etc. For this embodiment, data for a level includes, in addition to the coefficients, the number of partitions contained in the corresponding level and offsets to each individual partition. The offsets to the partitions identify the starting address for the coefficients in that partition. For example, the partition0[offset] in level 0 points to Partition 0 coefficient data (i.e., the coefficients for partition 0 in level 0). Accordingly, the source data file provides locations for each partition by identifying the level and the partition offset within the level for the coefficient data. Thus, the source data file permits the server to directly memory map partitions to partition locations in the source data file. As shown in FIG. 4, level "n" includes the coefficient data (e.g., level "n" is not partitioned).

Figure 5:
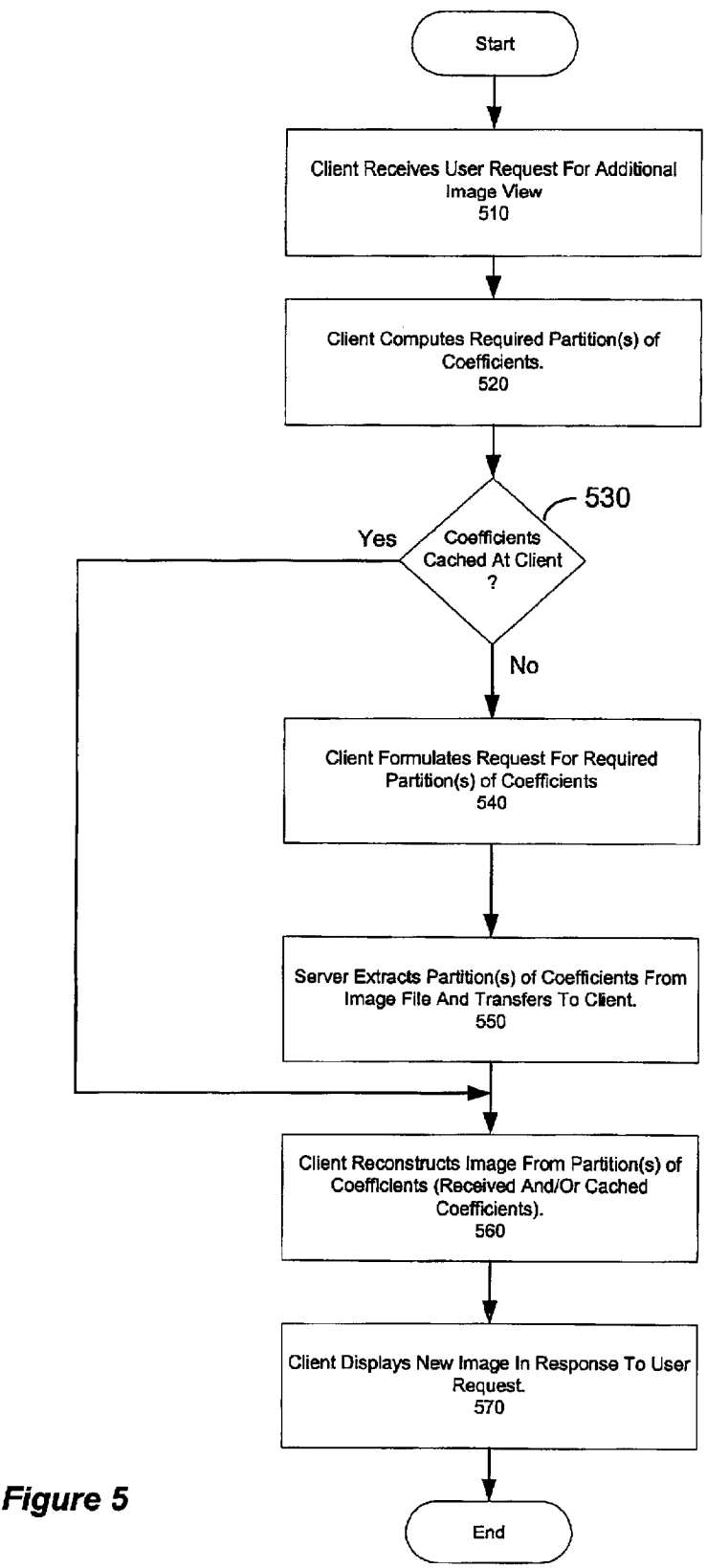
FIG. 5 is a flow diagram illustrating one embodiment for processing client requests for partitions of coefficients.

FIG. 5 is a flow diagram illustrating one embodiment for processing client requests for use with partitions of coefficients. A client application operates on a client computer that requires the display of source data, such as images. The process is initiated when the client computer receives a user request for additional source data. (Block 510, FIG. 5). In one embodiment, the user request for additional data is based on a user that requests to view additional image data. This request may be a request for a new image, a request to view a different portion of a currently displayed image, a request to view a currently displayed image at a greater resolution or a request to improve the quality of a currently displayed image. The client computes the required coefficients (Block 520, FIG. 5). If the coefficients to the request are stored at the client computer, then the client computer reconstructs the image from the user request from the coefficients cached (blocks 530 and 560, FIG. 5). If the coefficients are not cached at the client computer, then the client formulates a client request to the server for the requisite partitioned block(s) of coefficients (blocks 530 and 540, FIG. 5).

Upon receipt of the request, the server, using the source data file, identifies the location for the identified level(s), as well as the offset(s) to one or more partitions identified in the client request. In one embodiment, the server memory maps the entire image. Using the source data file, the server extracts partitions(s) of coefficients from the image file, and transfers the partitions(s) of coefficients to the client (block 550, FIG. 5). At the client, the image is reconstructed from either the coefficients received from the server or coefficients locally cached (block 560, FIG. 5). The client displays the new image in response to the user request (block 570, FIG. 5).

Quantization of Partitioned Coefficients

The techniques of the present invention apply to the use of quantization of partitions of coefficients. The quantization techniques have application for use when the network resources between the client and server are limited. For example, client 150 and client 160 of FIG. 3 may share network bandwidth. For this example, client 150 may consume, for a limited period of time, substantial network resources. During this time, client 160 is not allocated the necessary bandwidth to receive, in a reasonable period of time, non-quantized transform data from server 100. Under this scenario, client 160 requests quantized transform data. After client 160 gains access to an adequate amount of network resources, client 160 may request additional transform data necessary to reconstruct the source data at the full desired data integrity.

For the quantized embodiment, after the source data is transformed into the pyramidal data representation(s), the transformed data is quantized and is compressed. In one embodiment, to compress the transform data, one or more partitions of coefficients are quantized by an integer value. In one embodiment, partitions of coefficients are quantized by quantization bin widths, $Q_i$. There is one quantization bin width per coefficient block (i.e., one or more partitions of coefficients). Generally, this operation may be expressed as:

$$\hat{Q}\hat{W}\hat{I} = \hat{Q}R,$$

wherein, R represents a block of coefficients in the transform data, and $\hat{Q}$ represents the quantized function. For this expression, if truncation toward zero is used, the quantized function may be expressed as follows. If (R>0), then $$R_Q = \frac{R + .5Q}{Q}$$

else, (i.e., if R<0), $$R_Q = \frac{R - .5Q}{Q}$$

wherein, Q is an integer and the resultant is consistently truncated (i.e., either towards or away from zero), such that $R_Q$ is a multiple of the quantization bin width, Q. In one embodiment, the resultant is truncated towards zero.

In one embodiment, the partitions of coefficients are quantized in accordance with the corresponding level of the decomposition. Thus, for this embodiment, there is one quantization bin width, Q, for each level. For this embodiment, the quantization values may be quantized as follows:

$$R_{L1}^Q = \frac{R(Level1)}{Q1}$$

$$R_{L2}^Q = \frac{R(Level2)}{Q2}$$

$$R_{L3}^Q = \frac{R(Level3)}{Q3}$$

$$R_{LN}^Q = \frac{R(LevelN)}{QN}$$

wherein, "L" and "Level" represent the level of the decomposition for the "N" level example, and Q1, Q2, Q3 and QN represent quantization bin widths for the respective levels. Although the above expression represents quantization based on levels of the decomposition, any combination of different quantization values may be used to quantize a set of coefficients without deviating from the spirit or scope of the invention.

In one embodiment, the coefficients of the decomposition transform are quantized. For the embodiment that quantizes coefficients, the coefficients may be aggregated into a quantized coefficient block as follows:

$$R_{Level1}^Q = \frac{R(LH + HL + HH)}{Q1}$$

$$R_{Level2}^Q = \frac{R(LH + HL + HH)}{Q2}$$

$$R_{Level3}^Q = \frac{R(LH + HL + HH)}{Q3}$$

$$R^Q_{LevelN} = \frac{R(LH + HL + HH)}{QN}$$

Accordingly, for this example, the high-energy components for each coefficient block of the transform are quantized. Although the above example quantizes components of the transform in this manner, block of transform data may be aggregated and quantized in different ways.

The quantized coefficient block, $R^Q$, is compressed to generate the transmission coefficient block in accordance with the expression:

$$R^T = \hat{E} R^Q;$$

wherein, $\hat{E}$ defines the compression function, and $R^T$ defines the compressed coefficient block for transmission. In general, the compression function, $\hat{E}$, comprises a lossless coder. Any lossless encoding rule may be used for the compression function, $\hat{E}$, without deviating from the spirit or scope of the invention. For example, the compression function, $\hat{E}$, may be implemented with a Rice encoding function with no run length encoding, Huffman coding with run length encoding, arithmetic encoding, etc. In one embodiment, data not quantized (e.g., the low low ("LL") component of a level) is encoded using Rice encoder, and data quantized, which typically include runs of zeros, is encoded using an arithmetic encoder.

The compressed coefficient block, $R^T$, is transmitted to the client. At the client, the inverse quantization and decoder functions are executed. This operation may be expressed as:

$$R = \hat{Q}^{-1} \hat{E}^{-1} R_T.$$

The inverse transform, $\hat{W}^{-1}$ is performed on the coefficients to generate the original data.

Figure 6:
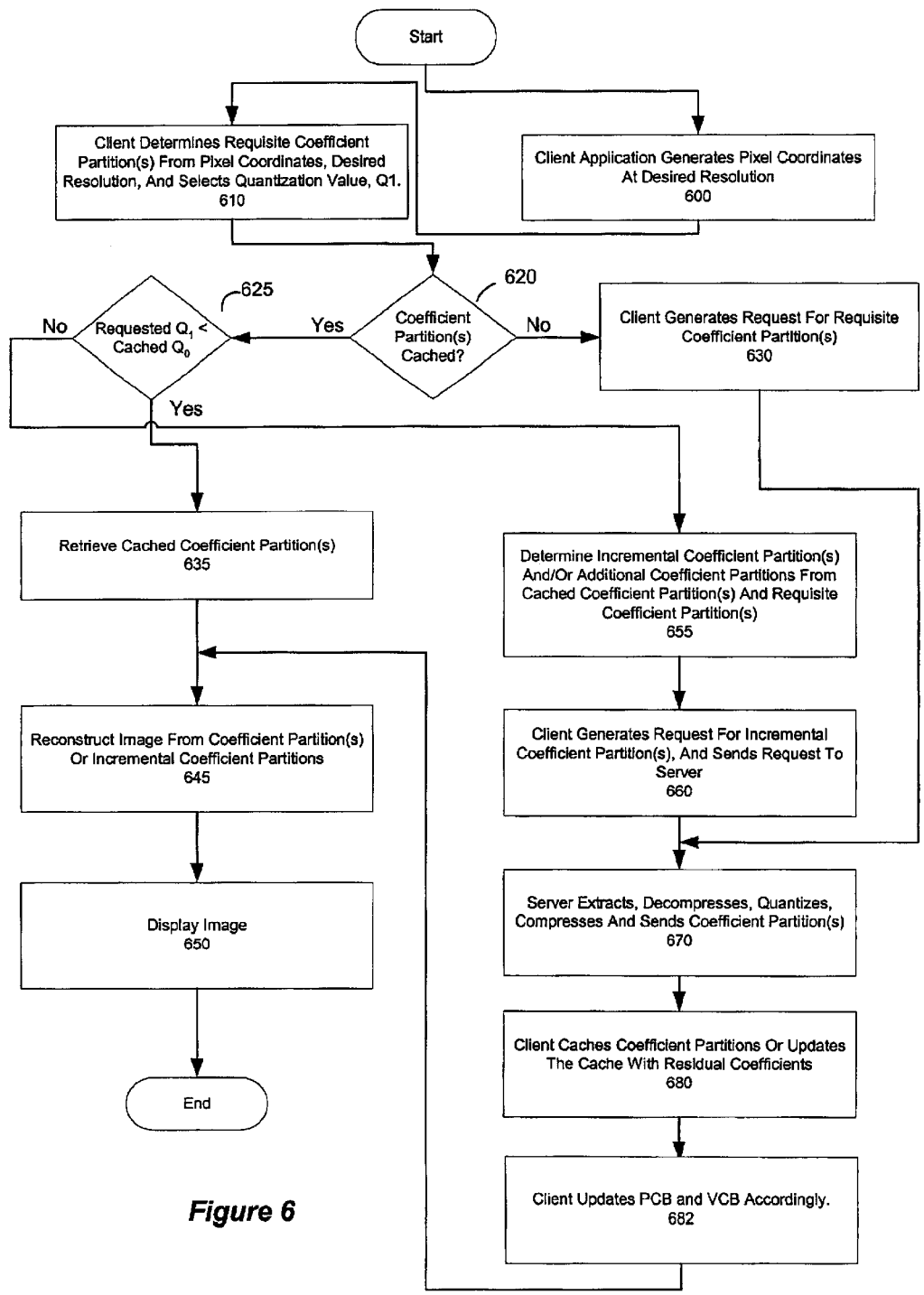
FIG. 6 is a flow diagram illustrating one embodiment for image transfer of quantized coefficients.

FIG. 6 is a flow diagram illustrating one embodiment for image transfer of quantized coefficients. The process is initiated when a client application generates pixel coordinates at a desired resolution for underlying source or image data (block 600, FIG. 6). From the pixel coordinates and resolution, the client determines the requisite coefficient partitions necessary to reconstruct the image. In addition, the client computer selects a quantization value, $Q_1$, to quantize the partitioned coefficients (block 610, FIG. 6). Typically, the selection of the quantization value is based on bandwidth restraints.

The client first determines whether the requisite coefficient partitions are cached locally (block 620, FIG. 6). If the requisite coefficient partitions are not cached at the client, then the client generates a request to the server for the requisite coefficient partitions (block 630, FIG. 6). If the requisite coefficient partitions are cached locally, then the client determines whether the level of quantization for the requested coefficients is less than the level of quantization for the cached coefficients (i.e., $Q_1 < Q_0$) (block 625, FIG. 6). If it is, then the client retrieves the cached coefficient partitions to reconstruct the image. The cached coefficient partitions are sufficient to reconstruct the image because they contain a sufficient amount of information to reconstruct the image (i.e., the level of quantization is greater so the amount of information contained in the partitions is less than the amount stored at the client) (block 635, FIG. 6). Alternatively, if the level of quantization for the requested coefficients is not less than the level quantization for the cached coefficients, then the client determines incremental coefficient partitions from the cached coefficient partitions and the requisite coefficient partitions (block 655, FIG. 6).

From this calculation, the client generates a request to the server for the incremental coefficient partitions, and transmits this client request to the server (block 660, FIG. 6).

The server receives the client request, for either the coefficient partitions or the incremental coefficient partitions, and the server extracts, decompresses, quantizes, compresses and sends the coefficient partitions identified in the client request to the client (block 670, FIG. 6). The client receives and caches the coefficient partitions or updates the cache with the residual coefficients. (block 680, FIG. 6).

In one embodiment, the client uses physical coefficients blocks and virtual coefficient blocks to track coefficients cached at the client. For this embodiment, the client additionally updates the status of the physical coefficient blocks and virtual coefficient blocks based on the coefficient partitions received (block 682, FIG. 6). In general, the physical coefficient blocks identify those partitions currently cached at the client. The physical coefficient blocks also include an address for the corresponding cached coefficient partition. The virtual coefficient blocks identify, if necessary, a level of quantization for at least a portion of a physical coefficient block (i.e., there may be multiple virtual coefficient blocks per physical coefficient block).

The client reconstructs the image from the coefficient partitions retrieved from the cache or the coefficient partitions, including incremental coefficient partitions, received from the server (block 645, FIG. 6). If the client receives incremental coefficient partitions, then the client aggregates the received incremental coefficient partitions into the requisite coefficient partitions, and then the client reconstructs the image from the requisite coefficient partitions. The client then displays the image (block 650, FIG. 6).

Figure 7A:
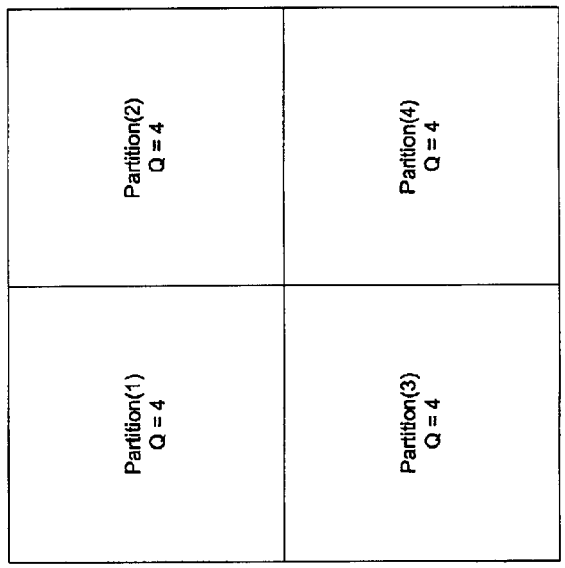
FIGS. 7a–c illustrate an example of tracking coefficient partitions at the client with physical and virtual coefficient blocks.
Figure 7B:
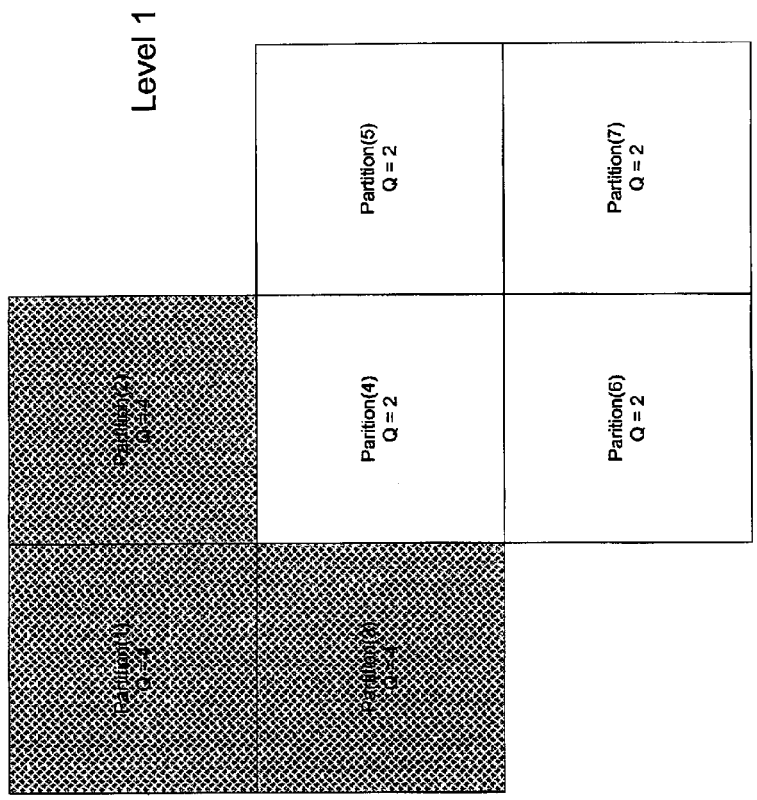
Figure 7C:
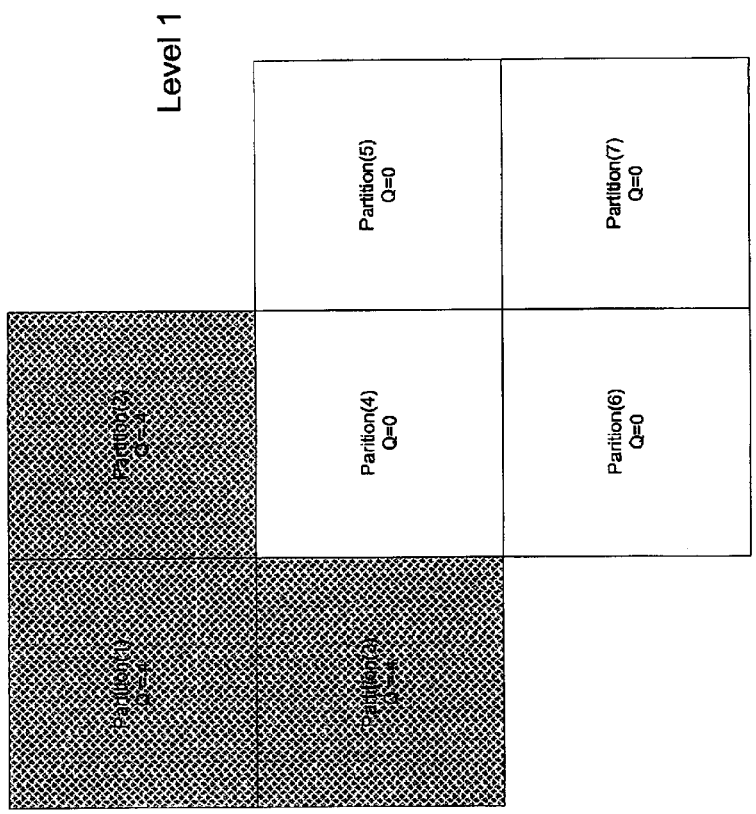

FIGS. 7a–c illustrate an example of tracking coefficient partitions at the client with physical and virtual coefficient blocks. For the example of FIG. 7a, the client receives four coefficient partitions, Partition(1)–Partition(4), all with a quantization value of four (4). For these partitions, the client tracks, in the physical coefficient blocks, the address of partition 1, partition 2, partition 3, and partition 4. For this embodiment, the client does not update the virtual coefficient block, but notes that all of the coefficient partitions have a quantization or Q value of four (4).

For the example of FIG. 7b, the client requests additional coefficient partitions from the server as well as a residual coefficient block. Specifically, for this example, the client receives coefficient partitions 5, 6 and 7, as well as the residual coefficients for partition 4 to decrease the level of quantization from 4 to 2. The client updates the physical coefficient blocks to reflect the cache address of new coefficient partitions 5, 6 and 7. In addition, the client stores information, in the virtual coefficient blocks, to identify the level of quantization, 4, for coefficient partitions 1, 2, and 3, and to identify the level of quantization, 2, for coefficient partitions 4, 5, 6 and 7.

An additional client request, illustrated in FIG. 7c, increases the resolution of partitions by decreasing the level of quantization to one (1). This example request does not require the client to update the physical coefficient block. The client updates the virtual coefficient block to reflect that coefficient partitions 4, 5, 6 and 7 received residual coefficient to improve the quality of the image to full resolution at that level.

Medical Imaging Application

Figure 8:
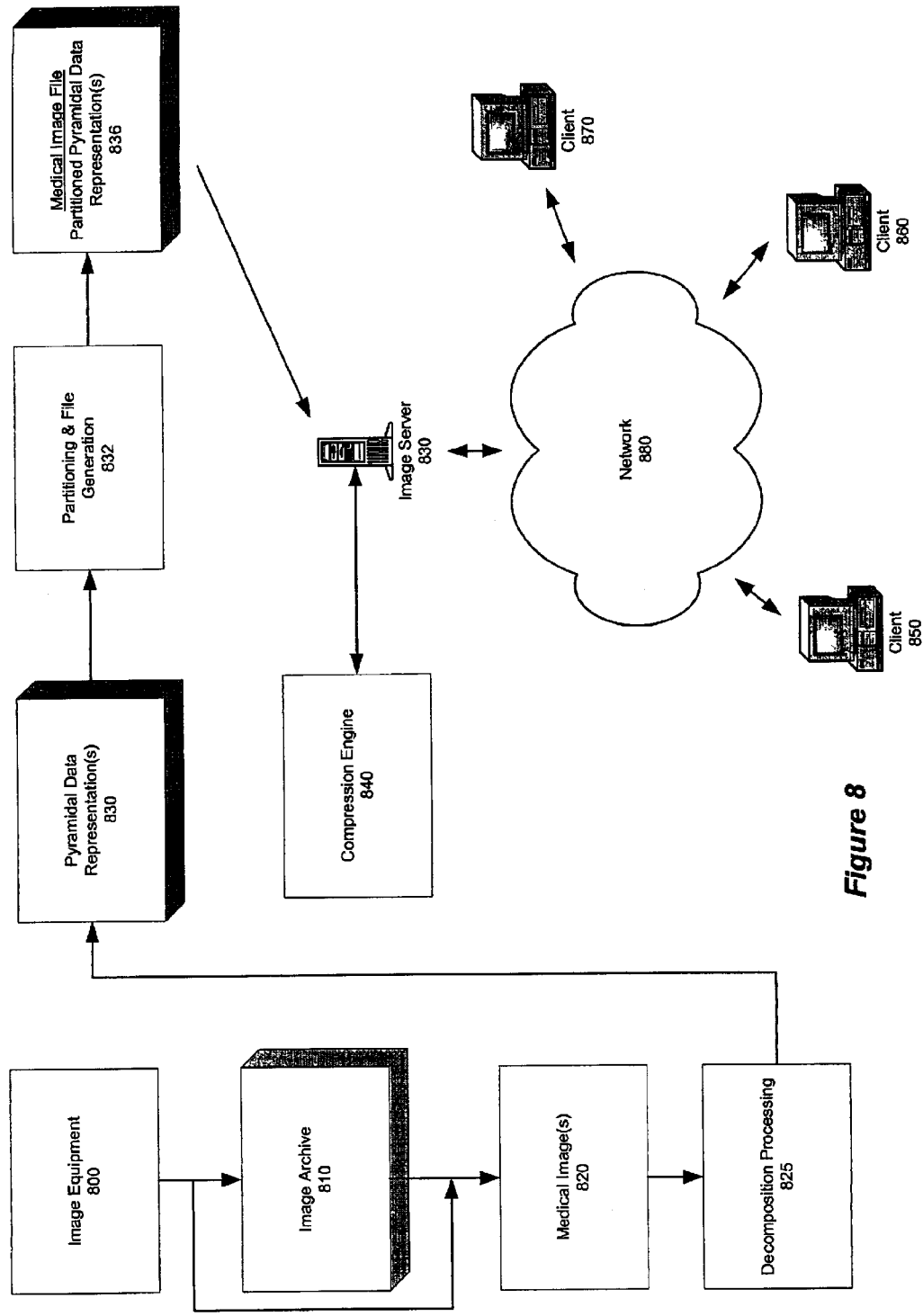
FIG. 8 is a block diagram illustrating one embodiment for use of the partitioned transform data in a medical imaging application.

FIG. 8 is a block diagram illustrating one embodiment for use of the partitioned transform data in a medical imaging application. For this embodiment, a medical imaging system optionally includes imaging equipment 800 to generate medical images 820 for optional storage in electronic form in an image archive 810. The image archive 810 contains electronic storage components such as disk drives and tape drives used to store the images in a highly reliable manner.

In one embodiment, after decomposition into the pyramidal data structure 130 and partitioned into a medical image file 136, the DICOM data is retained, and additional information specific to the image distribution system is augmented. The imaging equipment 800 includes any type of equipment to generate images, including medical equipment (e.g., X-ray equipment, CT scanners, and MR scanners).

For this embodiment, the medical imaging system includes at least one image server 830. As shown in FIG. 8, the image server 830 is coupled to a plurality of clients 850, 850 and 860. The medical images 820 are processed, by decomposition processing 825, to generate a pyramidal data structure 830. In addition, the partitioning & file generation processing 832 partitions the coefficients in the pyramidal data structure 830, and generates a medical image file, including header information to identify the levels of the coefficients and to identify the individual partitions within the levels.

Although the present invention has been described in terms of specific exemplary embodiments, it will be appreciated that various modifications and alterations might be made by those skilled in the art without departing from the spirit and scope of the invention.

What is claimed is:

1. A method for transferring source data from a server to a client, the method comprising the steps of;

generating, from the source data, transform data comprising spatially related coefficients such that a block of coefficients permit reconstruction of identifiable portions of the source data;

partitioning the transform data into a plurality of partitions of coefficients, each partition comprising coefficients for reconstruction of an identifiable portion of the source data;

generating, at a client, a request for at least one partition of the coefficients of the source data;

transferring, from the client to a server, the request;

extracting, at the server, the at least one partition of coefficients set forth in the request;

transferring, from the server to the client, the at least one partition of coefficients; and reconstructing the source data at the client from the transform data.

2. The method as set forth in claim 1, further comprising the steps of:

storing the partitions of coefficients in a permanent storage medium; and storing information to individually access the partitions of coefficients.

3. The method as set forth in claim 2, wherein:

the step of extracting, at the server, the partitions of coefficients set forth in the request comprises the step of obtaining the locations for the partitions of coefficients in the permanent storage medium; and the step of transferring from the server to the client the partitions of coefficients comprises the step of transferring the partitions of coefficients from the permanent storage medium to the client.

4. The method as set forth in claim 1, further comprising the steps of:

generating, at the client, the request to include at least one quantization value for the at least one partition of coefficients;

quantizing, at the server, the partitions of coefficients, in accordance with the quantization value; to generate quantized partitions of coefficients;

compressing the quantized partitions of coefficients to generate compressed partitions of coefficients; and de-compressing the compressed partitions of coefficients at the client to recover the partitions of coefficients.

5. The method as set forth in claim 1, further comprising the step of caching the partitions of coefficients at the client.

6. The method as set forth in claim 5, further comprising the steps of:

generating, at the client, a second request for the partition of coefficients from a prior request, the prior request including a first quantization value for the partition of coefficients and the second request including a second quantization value for the partition of coefficients;

transferring, from the client to a server, the second request;

extracting, at the server, the partition of coefficients identified in the second request;

quantizing, at the server, the partitions of coefficients in the second request, in accordance with the second quantization value; to generate second quantized partitions of coefficients;

generating a second compressed partition of coefficients from the second quantized partitions of coefficients;

transferring, from the server to the client, the second compressed partition of coefficients;

retrieving a first quantized partition of coefficients from the cache;

de-compressing the second compressed partition of coefficients to generate the second quantized partition of coefficients at the client;

generating a first and a second de-quantized coefficient blocks by multiplying the first and second quantized partition of coefficients by the first and second quantization values, respectively;

generating an aggregate partition of coefficients by adding the first de-quantized partition of coefficients with the second de-quantized partition of coefficients; and reconstructing the source data at the client from the aggregate partition of coefficients.

7. The method as set forth in claim 1, wherein the source data comprises a source image.

8. The method as set forth in claim 7, wherein the source image comprises a medical image.

9. A method for processing data at a server, the method comprising the steps of:

generating, from the source data, transform data comprising spatially related coefficients such that a block of coefficients permit reconstruction of identifiable portions of the source data;

partitioning the transform data into a plurality of partitions of coefficients, each partition comprising coefficients for reconstruction of an identifiable portion of the source data;

receiving, from a client, a request for at least one partition of the coefficients of the source data;

extracting, at the server, the partition of coefficients set forth in the request; and transferring, from the server to the client, the partition of coefficients.

10. The method as set forth in claim 9, further comprising the steps of:

storing the partitions of coefficients in a permanent storage medium; and storing information to individually access the partitions of coefficients.

11. The method as set forth in claim 10, wherein:

the step of extracting, at the server, the partitions of coefficients set forth in the request comprises the step of obtaining the locations for the partitions of coefficients in the permanent storage medium; and the step of transferring from the server to the client the partition of coefficients comprises the step of transferring the partition of coefficients from the permanent storage medium to the client.

12. The method as set forth in claim 9, further comprising the steps of:

receiving at the server, the request from the client to include at least one quantization value for at least one partition of coefficients;

quantizing, at the server, the partitions of coefficients, in accordance with the quantization value; to generate quantized partitions of coefficients; and compressing, at the server, the quantized partitions of coefficients to generate compressed partitions of coefficients.

13. The method as set forth in claim 9, wherein the source data comprises a source image.

14. The method as set forth in claim 13, wherein the source image comprises a medical image.

* * * * *